United States Patent [19]

Johnson, Jr. et al.

[11] 4,091,014

[45] May 23, 1978

[54] PROCESS FOR MAKING ETHER SULFONATES

[75] Inventors: Fred L. Johnson, Jr., Austin, Tex.; John A. Patterson, Fishkill, N.Y.

[73] Assignee: Texaco Development Corporation, New York, N.Y.

[21] Appl. No.: 746,563

[22] Filed: Dec. 1, 1976

[51] Int. Cl.² .................. C07C 143/42; C07C 143/11
[52] U.S. Cl. .......................... 260/512 R; 260/513 R; 260/612 D; 260/613 D
[58] Field of Search ................... 260/512 R, 513 R

[56] References Cited

U.S. PATENT DOCUMENTS 2,535,678  12/1950  Hollander et al. ............... 260/512 R Primary Examiner—Nicky Chan
Attorney, Agent, or Firm—Carl G. Ries; Thomas H. Whaley; James L. Bailey

[57] ABSTRACT

Covers a method of sulfonating organic alcohols to prepare ether sulfonates thereof by reacting said organic alcohol compound with a hydroxy-containing alkyl sulfonic salt thereof under carefully controlled conditions comprising use of a vacuum less than about 300 mm of mercury, while for at least the majority of the reaction period dispersing through the liquid reaction mass an inert gas.

34 Claims, No Drawings

PROCESS FOR MAKING ETHER SULFONATES

BACKGROUND OF THE INVENTION

1. Field of the Invention

This invention relates to an improvement of sulfonating organic compounds containing an alcoholic hydroxyl group to produce ether sulfonates useful as detergents and as surfactants for enhanced oil recovery processes.

2. Description of the Prior Art

Organic sulfonic acids and organic sulfonates are becoming increasingly important due to their use in the preparation of liquid detergents, particularly in the preparation of relatively salt-free detergents having good solubility characteristics. Even more recently, compounds of this general type have been found to be useful materials when employed as surfactants for enhanced oil recovery processes. In one general scheme sulfonated materials are prepared by sulfonation processes employing concentrated sulfuric acid or oleum. However, using such strong acids leads to the obvious problems of corrosion and/or salt disposal and separation following neutralization of the final reaction mixture to produce salt by-products. In most instances, products containing substantial amounts of the salt cannot be usefully employed, and such salt must be removed.

To obviate the above problems, another method of preparing organic sulfonates involves reacting an organic alcohol containing at least one hydroxyl group with a hydroxy-containing alkyl sulfonic acid salt. Under appropriate conditions, the two compounds are condensed with formation of by-product water to produce an ether sulfonate. A typical sulfonating (more properly sulfoalkylating) reagent here is sodium isethionate also named as the sodium salt of 2-hydroxyethane sulfonic acid.

In many instances use of hydroxy-containing alkyl sulfonic acids or salts such as 2-hydroxyethane sulfonic acid salt or other sulfonating reagents of this type involves one or more process difficulties. For example, in some instances the organic alcohol to be sulfonated and sulfonating reagent of this type are not mutually soluble one in another. As one example, the hydroxy compounds may be liquids at reaction temperatures but are not solvents for the solid, crystalline sulfonic acid salts. Hence, one is faced with a reaction system consisting of both liquid and solid phases with attendant obvious problems.

In still other instances, reactions of the above type are difficult to control or are even uncontrollable in many instances. Thus, for example, excessive foaming may occur which cannot be practically controlled or eliminated. It is important in controlling foaming to remove water by-product during the course of the reaction as such water is formed. However, resort to such well-known expedients as azeotropic distillation of said by-product water has been found to be unsuccessful or minimally useful.

In yet other processes involving the just described classes of reactants, prior art efforts were unsuccessful in that highly colored products were obtained. Yellow, brown or other colored products when used for detergent use, for example, are unsatisfactory. The discolored product requires bleaching in order to compete with like generally colorless products, which bleaching step adds considerably to the cost of production. In still other instances, sulfonation processes of this type involving the above reactants cannot be or are difficulty temperature controlled. Lastly, in some situations the proposed prior art sulfonating process cannot be adapted to batch, continuous, or semi-continuous processes, which latitude of choice is extremely desirable.

It is therefore a principal object of this invention to provide a process for the sulfonation of organic alcohols through reaction with hydroxyl-containing alkyl sulfonic acid salts, which process is free from the just-mentioned disadvantages of the prior processes.

A specific object of the invention is to provide a method of sulfonating organic alcohols via reaction with hydroxyl-terminated lower alkyl sulfonic salts such as the salt of 2-hydroxyethane sulfonic acid, which reaction can be controlled and produces the desired ether sulfonate products in relatively high yields.

The above-mentioned objects and advantages of the present invention will become apparent as the invention is more thoroughly discussed hereinafter.

SUMMARY OF THE INVENTION

In its broadest aspects the present invention comprises a method of sulfonating an organic compound having at least one alcoholic hydroxyl group which comprises the steps of reacting said alcoholic compound with a hydroxy-containing alkyl sulfonic acid salt by forming a reaction mass of said alcoholic compound and said sulfonic acid salt and carrying out said sulfonating reaction under a vacuum less than about 300 mm of mercury and for at least the majority of said reaction period continuously dispersing through said reaction mass an inert gas.

DESCRIPTION OF THE PREFERRED EMBODIMENTS

In more detail the practice of the present invention relates to a method of preparing ether sulfonates of the formula

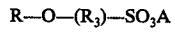

where R is a radical selected from the group consisting of $C_2$-$C_{22}$ alkyl, $C_2$-$C_{22}$ alkenyl, $C_2$-$C_{22}$ hydroxyalkyl, $C_2$-$C_{22}$ hydroxyalkenyl, alkaryl containing one or more $C_1$-$C_{18}$ alkyl groups substituted on said aryl group, aralkyl containing 7-28 carbon atoms, and polyether derivatives of any of the foregoing, $R_3$ is alkylene, and A is an alkali metal cation, which comprises the steps of forming a reaction mass by reacting ROH where R has the just stated significance with an alkali metal hydroxy-containing alkyl sulfonic acid salt under a vacuum less than about 300 mm of mercury while for at least the majority of said reaction period continuously dispersing an inert gas through said reaction mass.

In the most preferred embodiment of the invention, a process of making ether sulfonates of the formula

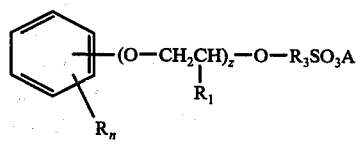

is carried out. Here R is a $C_1$-$C_{22}$ alkyl group, n is an integer of 1-3, $R_1$ is hydrogen or methyl, z is an integer of 1-40, $R_3$ is ethylene or propylene and A is an alkali metal cation. In this instance an alcoholic compound of the formula

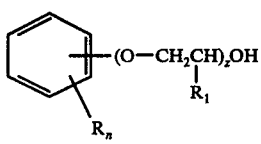

where R, $n$, $R_1$ and $z$ have a significance as just discussed is reacted with a compound of the $OHR_3SO_3A$ where $R_3$ and A are as just mentioned. Again, the reaction is carried out under proper vacuum control while dispersing an appropriate inert gas through the reaction mass.

The process of the present invention is adaptable to sulfonating a wide variety of organic compounds having at least one alcoholic hydroxyl group capable of reacting with an alkali metal hydroxyl-terminated alkyl sulfonic acid salt by way of condensation through respective hydroxyl groups. Such alcohols under the conditions of the process should be relatively non-volatile and therefore available for reaction in liquid form under vacuum. Usually they have a molecular weight greater than 200 and more often greater than 250. Fatty alcohols containing from about 8 to about 20 carbon atoms which may be sulfonated include such as lauryl alcohol, cetyl alcohol, tallow alcohol, octadecyl alcohol, and eicosyl alcohol.

Other non-volatile alcohols which may be sulfonated here include the so-called Oxo alcohols from the oxo process, vinylidene alcohols, Ziegler-type primary linear alcohols prepared from trialkylaluminum mixtures made by way of ethylene polymerization, subsequent oxidation, and hydrolysis of the resultant aluminum alkoxides as set out in U.S. Pat. No. 3,598,747 and other alcohols of this type. Typical vinylidene alcohols are set out in U.S. Pat. 3,952,068 and have the general structure

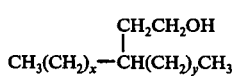

wherein individually, $x$ and $y$ are numbers from 1 to 15 and the sum of $x$ and $y$ is in the range of 6 to 16.

Polyhydric alcohols may also be employed in the process of the invention including such polyhydric alcohols as aliphatic polyhydric alcohols including the aliphatic glycols, such as, for example, the glycol ethers. Higher functionality polyhydric materials which may be employed include such as glycerol, sorbitol, trimethylolpropane, 1,2,6-hexanetriol, pentaerythritol and the like. Also, suitable are dihydric aromatic materials such as bisphenol-A and hydrogenated bisphenol-A. Preferred polyhydric alcohols are the aliphatic glycols having 10 or more carbon atoms and the aliphatic glycol ethers having from 10 to 20 carbon atoms.

Phenols and alkyl substituted phenols may also be employed here. Thus, for example, exemplary phenolic reactants include nonylphenol, dinonylphenol, cresol, and the like. Particularly preferred are alkyl substituted phenolic compounds falling within the following structural formula

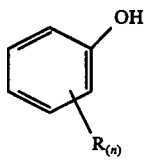

where R is preferably an alkyl group containing from 6 to 20 carbon atoms or a halo, nitro, or hydroxy alkyl substituted group of the same chain length, and n is an integer of 1, 2 or 3. Most typically R in the above formula is a $C_{8-12}$ alkyl group.

Another useful class of reactant alcohols here are those prepared by alkoxylating any of the above class of alcohols or others. Thus, the above compounds may be reacted with ethylene oxide, propylene oxide, butylene oxide or higher alkylene oxides having up to 18 carbon atoms or mixtures thereof. When mixed oxides are used, they may be added to the hydroxy or polyhydroxy compound either sequentially to form block polyether polyol compounds, or may be mixed and reacted simultaneously to form a random, or heteric oxyalkylene chain. The reaction of an alkylene oxide and a hydroxy or polyhydroxyl compound is well-known to those skilled in the art, and the basecatalyzed reaction is particularly described in U.S. Pat. Nos. 3,655,590; 3,535,307 and 3,194,773. If diols, triols, tetrols and mixtures thereof are alkoxylated polyether polyols may be obtained which have a molecular weight of from about 500 to about 10,000. These polyether polyols are well-known and may be prepared by any known process such as, for example, the processes described in Encyclopedia of Chemical Technology, Vol. 7, pages 257–262, published by Interscience Publishers, Inc.

A greatly preferred class of hydroxy reactants here include the compounds falling within the following formula:

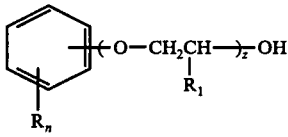

where R is a $C_1$–$C_{22}$ alkyl group and $n$ is an integer of 1–3, $R_1$ is hydrogen or an alkyl group of 1–18 carbon atoms, and $z$ is a number ranging from 1 to 40. Z more preferably is 1–10 and most preferably is 2–6. Preferably $R_1$ is hydrogen or methyl, $z$ is 1–10, and R is $C_6$–$C_{20}$, most preferably $C_8$–$C_{12}$.

Still other alcohols are aralkanols, preferably containing a total of from about 7 to about 28 carbon atoms. These may be represented by the following formula:

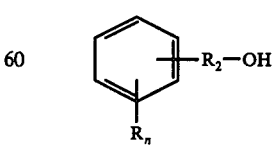

where $R_2$ is an alkylene group containing 1–22 carbon atoms, and R is a $C_1$–$C_{22}$ alkyl group and $n$ is an integer of 1–3. Polyether derivatives of these compounds may also be made by appropriate alkoxylation.

Thus, preferred alcohols which may be employed as reactants in preparing ether sulfonates are those having the general formula ROH, where R is a radical selected from the group consisting of $C_2$–$C_{22}$ alkyl, $C_2$–$C_{22}$ alkenyl, hydroxy or polyhydroxy derivatives of these alkyl or alkenyl compounds, alkaryl radicals containing one or more $C_1$–$C_{18}$ alkyl groups substituted on said aryl group, and aralkyl radicals containing 7-28 carbon atoms, and polyether derivatives of any of the foregoing.

The sulfonating agent used here is an alkali metal hydroxyalkyl sulfonic acid salt. Most preferably, the sulfonating agent is an alkali metal hydroxy-terminated straight chain alkyl sulfonic acid salt. Thus, the sulfonating agent employed here has the following structural formula:

$$OHR_3SO_3A$$

where $R_3$ is a straight or branched alkylene group, which optionally may contain other non-interfering groups such as halo, nitro, nitrile, etc. groups. More preferably, $R_3$ is a straight or branched chain unsubstituted alkylene group such as methylene, ethylene, propylene, butylene, pentylene, hexylene and higher alkylene groups. Most preferably, $R_3$ contains 1-4 carbon atoms, and in a greatly preferred embodiment is ethylene or propylene. A represents an alkali metal cation such as sodium, lithium, and potassium.

In a greatly preferred embodiment of the invention, the sulfonating agent, $OHR_3SO_3A$ is one where $R_3$ is ethylene or propylene, most preferably ethylene, and A is an alkali metal cation, most preferably potassium or sodium. The salts of such compounds are solid crystalline compounds whose addition to liquid organic hydroxyl compounds of the type described above causes severe process difficulties described in more detail hereinafter which are uniquely overcome by the invention here.

In carrying out the method of preparing the desired ether sulfonates, it is preferred that the vacuum expedient be such that the reaction is effected under a vacuum less than about 100 mm of mercury. In the most preferred embodiment, the process is carried out under a vacuum of 2-100 mm.

A wide variety of inert gases may be chosen as dispersing media, and their choice will be evident to those skilled in the art. Due to availability and cost, nitrogen is preferred. However, other gases such as argon, helium, xenon, etc. may be employed.

While the reactants may be mixed all at one time, and the reaction carried out as described generally above, it is greatly preferred that the sulfonic acid salt be slowly added to the alcohol to be sulfonated at a rate less than that sufficient to visibly agglomerate particles of the salt sulfonating agent during the reaction. Usually, this is carried out by adding in a slow manner an aqueous solution of the hydroxy-containing alkyl sulfonic acid salt to the organic alcohol at a rate such that large particles of the salt added to the alcohol, usually a liquid alcohol, are not noted during any of the reaction. Large particles if allowed to form quickly agglomerate to masses which tend to stick to the walls of the reaction vessel, agitator, etc., and materially lower conversion rates. Thus, it is important to add the sulfonic acid salt in a manner slow enough so that while visible particles are noted, yet the slurry of salt reactant, prior to its being consumed in the reaction is finely divided and reasonable uniformly sized such that the particles do not then agglomerate to larger entities.

In describing the process of the invention in more detail hereinafter for purpose of convenience, the organic reactant compound containing at least one alcoholic hydroxyl group will be termed "alcohol", and the hydroxy-containing alkyl sulfonic acid salt thereof will be referred to as "sulfonating agent". The product of the reaction will be simply referred to as "ether sulfonate".

With respect to reactant ratios, it has been found that ordinarily it is a preferred expedient to employ at least a slight excess of alcohol versus sulfonating agent. The excess alcohol present usually in liquid form acts as a "heat sink" during reaction, and may later act as a carrier for the product. Usually, from about 1.2 to about 2.5 moles of alcohol is present per mol of sulfonating agent, and more often the mol ratio is 1.5-2:1. However, in the broadest aspects of the invention aspects the molar ratio of alcohol to sulfonating agent can vary from 10:1 or higher to 1:2.

The reaction itself is base-catalyzed. Normally, a strong base is employed such as sodium hydroxide, and potassium hydroxide. Again, the amount of base utilized can vary widely. Usually, however, the ratio of base to alcohol varies from about 0.025:1 to 0.25:1. As a practical matter, the amount of base which one utilizes can be determined by the fact that if the base content is too low, an undesirably slow reaction results. On the other hand, if excess base is employed while a rapid reaction occurs, undesirable decomposition of the sulfonating agent may also result. One way of utilizing the base catalyst is to add the base along with sulfonating agent to the alcohol. However, it has been found greatly desirable to first form the alkoxide of the alcohol by addition of base thereto prior to addition of the sulfonating agent. The base may be added as a concentrated aqueous solution of say potassium hydroxide or sodium hydroxide in an amount sufficient to give the above mol ratio of base to alcohol. Preferably then the water added along with the base and the water produced by the formation of the alkoxide are removed before sulfonating agent is added. This may be done by heating the reaction vessel containing alcohol and base under conditions of vacuum and inert gas purge to remove the water and obtain a clear, dry solution of alkoxide in alcohol. Agitation is normally applied during this step and thereafter.

In a typical procedure the alcohol is charged to the reaction vessel, agitation applied, and alkoxide compound formed as just noted. Vacuum is applied and inert gas purge initiated. The nitrogen or other inert gas purge is introduced into the reactor vessel well below the liquid surface, preferably near the bottom of the kettle so that the gas is dispersed in the liquid as fine bubbles. The minute bubbles of gas have been found to have a dual purpose. They greatly assist in removing water of reaction as well as water added when an aqueous solution of sulfonating agent is employed. More importantly, the gas in some manner tends to moderate the reaction. Without benefit of gas, violent boiling occurs and mechanical carry-out of products and reactants takes place. The presence of gas dispersion tends to greatly dispel these objectional features, and prevent any substantial foaming during processing.

The volume of gas purge or flow rate will depend upon a number of factors including temperature of reaction, reactor vessel size, proportions of reactants, particular reactants employed, etc. Usually the flow rate is most dependent upon the size of the apparatus utilized. As one guide line, the volume of gas purge may be arrived at empirically by using that quantity of purge gas that will increase the pressure of the system (under vacuum) from full vacuum pressure with no purge to 30-60 mm mercury pressure with purge. In a typical case in a 1 liter laboratory kettle, the nitrogen flow rate is about 2 liters/min.

It has been found that both the combination of high vacuum and purge with inert gas are necessary to achieve a high product conversion. Without inert gas, for example, the above described condition of improper process control will occur. On the other hand, without utilization of the vacuum expedient low product conversion figures are obtained.

By utilizing vacuum and inert gas purge as described herein, one can realize product yields in terms of conversion of sulfonating agent greater than about 45%, and more often greater than 50%. In the usual case 55-75% of the sulfonating agent is converted to product. Most often that percentage is 60-70%, and in the optimum situation yields may be 70-80%.

Another process variant discovered important here is how the sulfonating agent is fed to the alcohol solution containing alkoxide catalyst. It has been found that the sulfonating agent should be fed, whether in solid or liquid form at a rate such that no large agglomerates of sulfonating agent are present in the reaction vessel. Usually, it is preferred that the sulfonating agent be fed as an aqueous solution containing 25-75 weight percent of sulfonate, more often 40-70 weight percent. Thus, for example, with respect to 2-hydroxyethane sulfonic acid, sodium salt, such material is fed as an aqueous solution to the alcohol at a rate such that the finally divided solid of sulfonating material (usually non-soluble in the alcohol reactant) is finely dispersed in the alcohol, with no large particles being allowed to occur. If water is not removed rapidly enough, the sulfonating agent agglomerates to a sticky mass by contact with water present, coats the reaction vessel and agitator means, materially reduces overall product conversion, and in many instances causes termination of the process.

The above mode of addition of sulfonating agent to alcohol must particularly be followed where the sulfonating agent is insoluble in the alcohol reactant. Usually, this is the case where a solid salt is employed. It has been found that not only is the sulfonating agent insoluble in the alcohol but usually no common solvent can be found which will mutually solubilize both reactants. Thus, it then becomes very important to follow proper directions of feeding to maintain the desired very small particle size of sulfonating reagent upon addition to alcohol during reaction.

The rate of feed of sulfonating solution to give a very fine dispersion of solid salt crystals in alcohol compound can again be empirically determined. For example, in a one liter glass kettle, the maximum rate is about 2-3 grams per minute of a 50-60% aqueous solution of sodium isethionate, while in a 5 gallon steam jacketed kettle, the maximum rate is about 10-20 pounds per hour of solution. As a general rule, the bigger the batch size of alcohol to be sulfonated the faster one can feed into said alcohol the sulfonating agent.

During addition of sulfonating agent to alcohol, usually the temperature is greater than 150° C in order to remove water added through the expedient of use of an aqueous solution of sulfonating agent, up to an upper limit of temperature necessary to prevent thermal decomposition of sulfonating agent. Usually, during addition of sulfonating agent to alcohol the temperature is maintained within a limit of 170°-200° C and more often is 170°-190° C.

Though, having some disadvantages, dry crystalline sulfonating agents usually in the form of a salt can be added to the alcohol following the same general reaction conditions outlined above. The major disadvantage to use of a solid sulfonating reagent appears to be difficulty in controlling proper small particle size distribution when adding to the alcohol. In addition, in many instances, the solid sulfonating agent is hygroscopic and hard to handle. Also, it has been noted that when a solid sulfonating agent has been used as a feed, before all the solid has had an opportunity to react, maximum conversion of already added material has occurred, and yields begin to decline with further heating.

After addition of sulfonating agent to alcohol has been completed in the manner generally outlined above, the actual reaction period or digestion period takes place with application of heat. The temperature of reaction should be as high as possible to effect a rapid complete reaction but should be less than the decomposition temperature of the sulfonating agent added in salt form. In those usual cases where the salt is a solid, whether added in solution or not, the temperature of reaction should be less than the melting point of the salt. Thus, for example, with respect to sodium isethionate the maximum temperature should be less than the melting point or approximately 190° C. In the usual case, then the temperature of reaction should be from slightly less than the melting point of salt to about 10°-20° C lower than that temperature. Again, with respect to sodium isethionate, the temperature of reaction should then be approximately 180°-190° C. Depending upon the sulfontaing agent used, and other process variables the temperature of reaction will usually fall between about 120° C and 250° C. and more often is 150°-250° C, most often 180°-250° C.

The digestion period or period of reactivity is carried out until the concentration of active ingredient (A.I.) has reached a maximum, at which time the reaction is quenched. It has been found that the concentration of active ingredient after reaching a maximum begins unexpectedly to materially decline. Thus, it is important to terminate the reaction after maximum conversion is reached. It is thought, that some type of decomposition occurs here or that the active product reacts further to a non-active product.

In order to terminate the reaction when the A.I. has reached a maximum, the preferred procedure is to monitor the course of the reaction during the digestion period by titrating samples periodically for A.I. content. In this manner, the reaction can be stopped when the A.I. content is at or near its maximum value. One method of analysis to determine A.I., particularly applicable to those sulfonates with a chain length of $C_8$ or greater involves a 2-phase titration with mixed indicators. Essentially a solution of anionic surfactant is titrated with a standard solution of a quaternary ammonium cationic salt in the presence of mixed indicators (dimidium bromide and disulfine blue) in a 2-phase (aqueous:chloroform) titration system.

In more detail this titration procedure is run as follows:

1. Weigh approx. 1 g sample into a 150-ml beaker by smearing it on the sides of the beaker. Drop in a magnetic stirring bar.
2. Pipet in 100 ml of 10% (V/V) ethyl alcohol in water.
3. Dissolve the sample with stirring.
4. Transfer an aliquot (2 to 5 ml) to the titration bottle.
5. Add water from a graduated cylinder to bring the sample aliquot to 5 ml.
6. Add:
   (a) 10 ml 10% $Na_2SO_4$ solution.
   (b) 5 ml of acid indicator sol.
   (c) 15 ml of chloroform.
7. Titrate with standard Hyamine 1622 until bottom phase turns from pink to blue and all traces of purple are gone.
8. Calculate AI in meq/g or % as follows:

$$AI, meq/g = \frac{ml\ Hyamine \times N\ Hyamine \times 100}{ml\ Sample\ Aliquot \times Sample\ Wt.}$$

AI, % = (AI, meq/g)×(meq. wt. surfactant)×(100)

The amount of time to reach maximum conversion will vary widely depending upon the reactants employed, temperature of reaction, reaction mass size, etc. As a guideline it usually takes ½-1 hour to complete a small laboratory preparation say 1 liter. Scaling up to a five gallon batch usually involves a reaction time of 2-4 hours, while carrying out reaction in a 2,000 gallon reactor takes approximately 6-7 hours. Time of reaction then may vary from about ¼ hour to about 24 hours.

After maximum conversion is reached by measurement of A.I. content, the reaction mass is cooled. By cooling, decrease in A.I. content is reduced or substantially prevented and, in addition, any loss in A.I. content caused by hydrolysis of product when subsequently diluted with water is kept to a minimum. If a hot reaction mass is diluted to prepare product in a final diluted form suitable for use, A.I. losses can run as high as 10-20% upon dilution. It has also been found that one may slow the rate of decrease in A.I. content by breaking the vacuum (but retaining the inert gas purge) after maximum conversion has been obtained.

After completion of the reaction as noted above, usually the reaction mass is diluted. In most instances, the dilution water is first acidified to give an essentially neutral diluted final product.

As a last step in the process, and in a preferred embodiment, product extraction is carried out. It has been found that in order to separate the ether sulfonate product from unreacted or excess alcohol a water-organic ester such as ethyl acetate system or an organic ketonehydrocarbon-water extractant solvent system may be most usefully employed. The last mentioned solvent system preferably is a mixture of benzene, acetone and water. In first attempted purifications of product, it was originally found that fractionation by use of immiscible organic solvents was not satisfactory. On the other hand, when water was used many solvents also employed were emulsified by the sulfonated surfactant products. However, by use of the just mentioned mixtures, good separation was achieved, as will be shown hereinafter in more specific detail.

With respect to use of an inert gas purge, it is interesting to note that merely blanketing the reaction with an inert gas or putting a pad of inert gas such as nitrogen over the liquid reaction mass had no affect in properly controlling the reaction, as compared to the dispersion method described in great detail above. Along this line it should also be noted that resort to some type of azeotropic distillation by removing water of reaction and extraneous water added was not an appropriate technique to properly carry out the process of this invention. Only by resort to vacuum-inert gas feed control can one achieve proper maximum conversion in terms of A.I. and conversion of starting sulfonating agent.

The following examples specifically illustrate the process of the invention. It should be understood, of course, that these examples are merely illustrative and that the invention is not to be limited thereto.

EXAMPLE 1

In this run, which typified the process of the invention, the apparatus consisted of a 1-liter glass resin kettle and heating mantle, the kettle being outfitted with a stirrer, thermometer, temperature controller, and dip leg extending almost to the bottom of the kettle. Aqueous sulfonating solution and nitrogen purge (approximately 2 liters/min) were both metered to the kettle through the dip leg. Gaseous effluent from the kettle (nitrogen and water vapor) pass through a Vigreaux column which served as a disengaging zone to prevent carry-over of liquid kettle contents during feed of sulfonating agent. From the top of the Vigreaux column, the vapors passed through a water cooled condenser into a wet ice trap, and thence into a dry ice trap ahead of the vacuum pump.

The alcohol sulfonated in this instance was

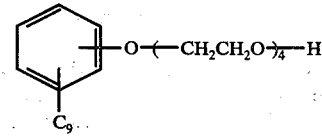

Specifically, 771.5 grams (1.95 mols) was charged to the kettle, and thereafter the stirrer started. To the alcohol was added a 50% KOH solution in an amount equivalent to 10.92 grams KOH or 0.195 mols. Thereafter the kettle was heated and evacuated which continued until the kettle temperature reached 185° C and pressure was adjusted to approximately 40 mm by means of the nitrogen purge.

To the above was then fed sodium isethionate solution. A total of 339 grams (1.30 mols) of a 56.7% solution was added. The sulfonating agent was fed at approximately 1-2 grams/minute rate. In this particular run, the sulfonating agent feed required 3 hours and 25 minutes at an average rate of 1.65 grams/minute. The mole ratio of alcohol to sulfonating agent was 1.5:1 and the mole ratio of potassium hydroxide to alcohol was 0.1:1.

After all the sulfonating agent had been fed over the above period of time, the pressure was reduced to 20-30 mm while maintaining the nitrogen purge. During this digestion or reaction step, the temperature was maintained at about 185° C and samples were taken periodically from the kettle to determine an active ingredient (A.I.) analysis. Thirty-five minutes after the sulfonating agent feed was ended the A.I. content was 53 weight percent, and the conversion in terms of sulfonating agent was approximately 75%. The conversion in terms of alcohol was 50%.

EXAMPLE 2

This example was run as in Example 1 with the exception that the alcohol was heated under vacuum to 180° C at 20 mm pressure before the potassium hydroxide solution was added. With respect to amounts of reactants, 377 grams (0.95 mols) of alcohol and 178 grams (0.722 mols) of sulfonating agent were employed. The sulfonating agent was in the form of a 60% solution. With respect to KOH, 5.1 grams or 0.09 mols were utilized. The molar ratio of potassium hydroxide to alcohol was 0.095.

Twenty-four minutes after the sulfonating feed was ended, the A.I. content was 57 weight percent, the sulfonating agent conversion was 81% and the alcohol conversion was 61%.

EXAMPLE 3

Here the procedure of Example 1 was followed with the exception that the alcohol was

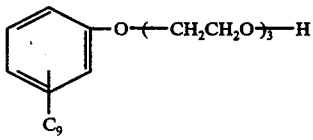

Specifically, with respect to amounts of reagents employed, 624 grams (1.79 mols) of alcohol were reacted with 294 grams (1.19 mols) of sulfonating solution. The potassium hydroxide solution was used in an amount of 16 grams (0.13 mols) based on dry potassium hydroxide. The molar ratio of alcohol to sulfonating agent was 1.5 and the molar ratio of potassium hydroxide to alcohol was 0.075.

1.25 hours after the sulfonating agent feed was ended the A.I. content was 58.4 weight percent, the sulfonating agent conversion was 92% and the alcohol conversion 61%.

EXAMPLE 4

Here the procedure of Example 1 was followed with the exception that the alcohol was

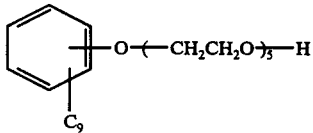

444 grams (1.0 mols) of alcohol were reacted with 197 grams (0.80 mols) of sulfonating solution. 6 grams of potassium hydroxide solution (0.05 mols) was utilized as the base catalyst. The mol ratio of alcohol to sulfonating agent was 1.25, and the mol ratio of potassium hydroxide to alcohol was 0.05.

One hour after the sulfonating agent feed was terminated, the A.I. content was 54 weight percent, the conversion of sulfonating agent was 74% and the conversion of alcohol was 59%.

EXAMPLE 5

The same apparatus and the procedure of Example 1 was used with exception that the alcohol employed was as follows.

$$R_4O\text{-}(CH_2CH_2O)_3\text{-}H$$

where $R_4$ represents a $C_{16}$-$C_{18}$-$C_{20}$ straight chain alkyl group blend.

500 grams (1.12 mols) of alcohol were reacted with 222 grams (0.90 mols) of sulfonating solution. 10 grams of KOH solution (0.084 mols) was employed here. The molar ratio of alcohol to sulfonating agent was 1.25 and molar ratio of KOH to alcohol 0.075.

EXAMPLE 6

The process of Example 1 was followed with the exception that the alcohol used was

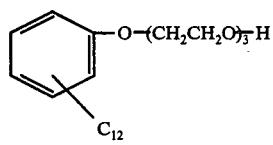

500 grams (1.27 mols) of alcohol was reacted with 155 grams of sulfonating solution (0.623 mols). The potassium hydroxide solution was used in an amount of 16 grams (0.094 mols). The molar ratio of alcohol to sulfonating agent was 2.0, and the molar ratio of KOH to alcohol was 0.074 mols per mol of alcohol.

Three hours after the sulfonating acid feed was terminated, the A.I. content was 43 weight percent. The conversion here in terms of sulfonating agent was 77% and the alcohol conversion was 38%.

EXAMPLE 7

Here, the versatility of the process was illustrated in that dry sodium isethionate was employed. Specifically, the procedure of Example 1 was followed with the exception that at about 100° C kettle temperature, dry sulfonating agent was added. Thereafter, the procedure was the same as in Example 1.

Specifically, 682 grams (1.72 mols) of alcohol was reacted with 148 grams (1.0 mol) of a dry sulfonating agent. The amount of potassium hydroxide (50% solution) used was a 9.9 grams (equivalent to 0.15 mols KOH). The molar ratio of alcohol to sulfonating agent was then 1.72 and the molar ratio of KOH to alcohol was 0.087.

Two hours after the kettle temperature had reached 185° C the maximum A.I. content was 48 weight percent. The sulfonating agent conversion was 74% and the alcohol conversion was 43%.

In yet another run similar to the above powdered KOH was utilized instead of a solution. Results were exactly the same as above except the maximum A.I. was reached in 1 and ½ hours instead of 2 hours.

EXAMPLE 8

This run was carried out using the general procedure of Example 1 with the exception that a 5 gallon stainless steel, steam jacketed kettle was the apparatus employed. Nitrogen and sulfonating agent feeds entered the kettle together through a bottom opening rather than through a dip leg. The sulfonating salt solution feed rate averaged 6.0 lbs/hr.

25.00 lbs. (28.64 mols) of alcohol was reacted with 10.99 lbs. 19.10 mols) of sulfonating solution. The amount of potassium hydroxide solution was 0.84 lbs. (2.89 mols). The molar ratio of KOH to alcohol 0.1.

The maximum A.I. content reached was 51.4 weight percent found 3.75 hours after ending the sulfonating agent feed. The sulfonating agent conversion was 72% and alcohol conversion was 48%.

EXAMPLE 9

Here the procedure of Example 1 was followed except no vacuum was employed. The sulfonating feed solution was dropped into the kettle from a dropping funnel and 220 grams (0.55 mols) of alcohol was reacted with 74 grams of sulfonating solution (0.50 mols). The potassium hydroxide solution was used in an amount of 2.8 grams (0.05 mols) with a molar ratio of alcohol to sulfonating solution being 1.1, and the molar ratio of potassium hydroxide to alcohol being 0.09.

4 and ¾ hours after the sulfonating feed was ended only 55% of the sulfonating agent was converted versus the 75% conversion in Example 1.

EXAMPLE 10

Here, the importance of using the proper reaction temperature is illustrated with respect to obtaining optimum results, particularly in terms of maximum sulfonating agent conversion.

The procedure of Example 4 was followed with the exception that the kettle temperature was 170°–179° C.

Specifically, 555 grams of alcohol (1.25 mols) was reacted with 247 grams of sulfonating agent solution (1.0 mol). 8 grams of potassium hydroxide solution (0.0625 mols) was employed. The molar ratio of alcohol to sulfonating agent was 1.25 and molar ratio of potassium hydroxide to alcohol was 0.05.

5 and ¾ hours after the sulfonating agent feed was ended the maximum A.I. content was obtained in an amount of 47.3 weight percent. The alcohol conversion was 52%. More importantly the conversion in terms of sulfonating agent was 65% versus the 74% figure of Example 4.

EXAMPLE 11

Here again a reaction temperature was chosen outside the recommended maximum. Particularly, in this instance the temperature of reaction was above the melting point of the particular sulfonating agent. The procedure of Example 1 was followed with the exception that the temperature was maintained at 210°–212° C.

Specifically, 600 grams (1.5 mols) of alcohol was reacted with 24 grams (1.0 mol) of sulfonating agent solution. Six grams of potassium hydroxide solution (0.051 mols) was employed. The molar ratio of alcohol to sulfonating agent was 1.5 and the molar ratio of potassium hydroxide to alcohol was 0.034.

In this instance the maximum A.I. content found was that taken in a sample 12 minutes after the sulfonating agent feed was ended. This sample had a 39 weight percent A.I. The conversion in terms of sulfonating agent was 61% and the alcohol conversion was 41%. These figures should be compared to the markedly more favorable results of Example 1.

EXAMPLE 12

This example was a direct comparison of operating with and without use of vacuum in both cases using a nitrogen purge.

The apparatus of Example 8 was utilized with the procedure being as follows. The alcohol was charged to the kettle and agitation initiated. Thereafter, potassium hydroxide solution was added, and heating initiated along with vacuum to remove both water added with the potassium hydroxide and the water of reaction between the alcohol and potassium hydroxide. When all water was removed, the kettle was heated to 185° C under 4 mm of pressure. The solution of sodium isethionate along with nitrogen purge was fed in the bottom of the kettle at a rate of approximately 10 pounds per hour. After all the sulfonating agent had been fed in, the vacuum was broken and digestion carried out at atmospheric pressure at a temperature of 185° C with nitrogen purge.

22.5 pounds (25.5 mols) of alcohols were reacted with 16.8 pounds (31.9 mols) of sulfonating agent solution. The amount of potassium hydroxide solution employed was 0.22 pounds (1.78 mols). The molar ratio of alcohol to sulfonating agent was 0.80 and the molar ratio of potassium hydroxide to alcohol was 0.07.

After 22 hours digestion at atmospheric pressure, the A.I. content increased to a maximum of 21.8%. The conversion in terms of sulfonating agent was 19%, and conversion in terms of alcohol was 24%.

After the above digestion at atmospheric pressure, the reaction vessel was again evacuated with nitrogen purge to 20-50 mm and the reaction run for an additional 7 hours at 185° C. After this additional reaction time under vacuum, the A.I. increased to 52.5 weight percent. The conversion of sulfonating agent was 45% and that of alcohol was 57%.

EXAMPLE 13

Here, the general procedure of Example 8 was followed with the exception that the feed rate of the sulfonating solution was 5 pounds per hour.

However, instead of following the preferred procedure of gradually cooling the hot kettle product before dilution, the product here at a temperature of approximately 180°–185° C was discharged into an approximate 25° C water. It was noted that a severe loss of A.I. occurred upon dilution due to hydrolysis of the hot alkaline kettle product.

Specifically, 21.44 pounds (24.50 mols) of alcohol was reacted with 10.74 pounds (19.59 mols) of sulfonating agent. The amount of potassium hydroxide solution employed was 0.70 pounds (2.45 mols). The molar ratio of alcohol to sulfonating agent was 1.25 and the molar ratio of potassium hydroxide to alcohol was 0.10.

Three hours after the sulfonating agent feed was ended the A.I. content was 54 weight percent, the sulfonating agent conversion was 66% and the alcohol conversion was 53%.

The kettle product was diluted while hot into water to make up a 25.4% solution. Basis the 54% A.I. in the neat kettle product, the diluted product should have had a 13.7% A.I. However, titration of the diluted product showed only a 11.3% A.I., representing a 17.6% loss of A.I. upon dilution hot.

EXAMPLE 14

This run was made exactly as in Example 13 with the exception that the kettle product was cooled to 92° C before discharging into the room temperature water. The loss in A.I. due to a hydrolysis upon dilution was greatly reduced compared to the results in Example 13.

Specifically, 25.00 pounds (28.66 mols) of alcohol was reacted with 10.99 pounds (19.12 mols) of sulfonating solution. The potassium hydroxide solution employed was 0.90 pounds (2.86 mols). This gave a mol ratio of alcohol to sulfonating agent of 1.50 and a mol ratio of potassium hydroxide to alcohol of 0.10.

The A.I. content of the kettle product reached 49.9 weight percent 3 hours after the sulfonating agent feed was ended. Conversion in terms of sulfonating agent was 80% and in terms of alcohol was 54%.

The kettle product was cooled to 92° C then discharged into water to make a 19.3% solution. Basis the dilution factor, the A.I. content of the diluted product should have been 9.64%. Titration of the diluted product showed 9.2% A.I. for a loss of A.I. of only 4.6%.

EXAMPLE 15

Here, a sulfonation was attempted using vacuum only with omission of nitrogen purge. The apparatus and procedure used was the same as in Example 1.

693 grams (1.75 mols) of alcohol was reacted with 304 grams (1.16 mols) of sulfonating solution. Twenty-two grams of potassium hydroxide solution was used equivalent to 0.175 mols potassium hydroxide. The mol ratio of alcohol to sulfonating agent was 1.50, and the mol ratio of potassium hydroxide to alcohol was 0.1.

No numerical results in terms of product were obtained. In the absence of the nitrogen purge uncontrollable violent boiling and bumping occurred. After 15 minutes of adding sulfonating agent feed, most of the kettle contents had been carried overhead through the Vigreaux column on top of the kettle, and were caught in traps.

It is obvious therefore that the sulfonating reaction described here contemplates use of a nitrogen purge, without which the reaction cannot be run in a practical manner.

EXAMPLE 16

Here, a prior run was made using the conditions described in U.S. Pat. No. 2,535,678 which disclosed for the first time use of sulfonating agents of the type envisioned here. Specifically, Example 7 of this patent was followed. In this example a 2 mol ethoxylate of diisobutylphenol was used as an alcohol source. Here, for purposes of comparison a similar material, the 4 mol ethoxylate of nonylphenol was employed following the above patented directions.

The apparatus used consisted of a 1-liter glass resin kettle, heating mantle, stirrer, thermometer, temperature controller, nitrogen inlet tube, Dean-Stark trap, and aspirator for vacuum.

The procedure used was to mix the alcohol, dry sulfonating agent, powdered sodium hydroxide and xylene in the kettle. Threreafter, nitrogen purge was started through the kettle and stirring and heating initiated. The reaction mixture was heated until good reflex of xylene occurred at a kettle temperature of approximately 160° C. Heating at reflux temperature was continued for 7-8 hours, after which time xylene was removed under vacuum and the kettle temperature allowed to increase to 178° C. At this time a sample was taken, and it was found that only a trace of A.I. was found in the kettle product.

The mol ratios of reactant were used as directed in Example 7 of the above patent, and specifically were 0.83 with respect to alcohol:sulfonating agent and 0.075 with respect to sodium hydroxide to alcohol. 396 grams of alcohol (1.0 mols) and 178 grams of sulfonating agent (1.2 mols) were heated in the above procedure. Three grams of powdered sodium hydroxide were also employed (0.075 mols) along with 250 grams of xylene.

EXAMPLE 17

Here, Example 6 of U.S. Pat. No. 2,535,678 was followed with the exception that the 4 mol ethoxylate of nonylphenol was substituted for the 2 mol ethoxylate of diisobutylphenol.

The apparatus of Example 16 was employed with the exception that a steam jacketed condenser was used instead of a Dean-Stark trap.

Again the same mol ratios suggested in Example 6 of the above cited patent were employed, namely, a mol ratio of alcohol to sulfonating agent of 0.83 and a mol ratio of sodium hydroxide to alcohol of 0.075.

396 grams (1.0 mol) of alcohol, 178 grams (1.2 mols of sulfonating agent, and 3 grams (0.075 mols) of powdered sodium hydroxide were mixed in the kettle, stirred, purged with nitrogen and heated to 165°–175° C. Nitrogen and water vapor were allowed to excape through the steam jacketed condenser, and the reaction held at 165°–175° C for 2 hours. Temperature was then increased to 174°–177° C for 20 hours. While the particular patent example called for holding at this temperature, for 13 hours, after 10½ hours the A.I. was only 9.7% so the reaction was allowed to go 20 hours.

Results after 10½ hours at 174°–177° C gave an A.I. of 9.7%. After 20 hours at 174°–177° C, the A.I. was 21.3 weight percent, the sulfonating agent conversion was 19%, and the alcohol conversion was 23%.

EXAMPLE 18

This example illustrates the desirability of carefully dispersing the sulfonating agent by slow feed addition in a controlled manner, whether fed to the alcohol by way of solution or solid.

Here 455 grams (1.15 mols) of the alcohol of Example 1, and 174 grams (.677 mols) of sodium isethionate were reacted along with 6.6 grams (0.1 mol) of potassium hydroxide pellets. The mol ratio of alcohol to sulfonating agent was 1.72, the mol ratio of potassium hydroxide to alcohol was 0.09.

In this instance, the alcohol, sulfonating solution and potassium hydroxide pellets were all added together and mixed in the reaction kettle. The water was carefully removed by heating, evacuating and purging with nitrogec. The temperature and pressures were adjusted as in Example 1 with the apparatus also being the same.

Approximately 1 hour after the water removal was begun it was noted that the sulfonating agent began to stick to the bottom and walls of the kettle as well as the stirrer, thermometer and dip leg in the form of a sticky mass. No sulfonating dispersion was obtained. After 5.5 hours at 185° C and 30 mm pressure, the A.I. content reached a maximum of 41.1%. When the run was terminated after 7.25 hours at 185° C and 30 mm pressure, some solid sulfonating agent remained in the kettle. The A.I. content had dropped to 35.6% despite the presence of unreacted sulfonating agent in the kettle. Basis the maximum A.I. content achieved, the conversion in terms of sulfonating agent was only 64% and in terms of alcohol was only 42%. Sulfonating agent conversion was thus well below that obtained when the particular process parameter of proper dispersion of sulfonating agent in the reaction mass during addition and initial reaction is followed.

EXAMPLE 19

Here, the procedure and apparatus of Example 1 was employed. However, in this instance a solution of 2- hydroxypropanesodium sulfonate was employed. The kettle temperature during this run was 166°–177° C due to the fact that this particular sulfonating agent is not as stable as the next lower homolog employed in Example 1.

Specifically 594 grams of the alcohol of Example 1 (1.5 mols) was reacted with 324 grams (2.0 mol) of the 2-hydroxypropanesodium sulfonate used as a 50% solution. Twenty grams of potassium hydroxide solution were also employed (0.15 mols). The mol ratio of alcohol to sulfonating agent was 1.5 and, the mol ratio of potassium hydroxide to alcohol was 0.1. After 2.2 hours beyond termination of sulfonating agent feed, the A.I. content reached a peak of 20%. The conversion in terms of sulfonating agent was 28%, and the alcohol conversion was 19%. Thus, it can be seen that the process of the invention is adaptable to a variety of sulfonating agents falling within the broadly defined class above, through the most preferred reagent is the 2-hydroxyethane sulfonic acid salt.

EXAMPLE 20

Here, one preferred method of separating the ether sulfonate reaction products of the invention from starting material is shown.

A simulated reaction product consisting of 25% sodium isethionate, 25% of the product of Example 1 (about 80% pure, made by sulfation/sulfonation of the alcohol starting material of Example 1), and 50% of the alcohol reactant of Example 1 using weight/volume ratios listed in Table I below was treated first with an organic solvent (listed under A) to precipitate principally sodium isethionate which is filtered off. The filtrate was diluted with water and optionally a third solvent was added. Organic and inorganic layers were separated and the solvents removed by evaporation. Results are given in Table I below. As can be seen the ethyl acetate-water and acetone-benzene-water combinations were the best, and less prone to emulsify and foam than other solvents employed as extractants.

two distinct layers were formed, the top layer being ethyl acetate-rich and the bottom being water-rich. The layers were separated and most of the solvents removed by evaporation. From the ethyl acetate solution was obtained 4.38 parts which was essentially recovered alcohol. After concentration of the water-rich layer to 33.88 parts, the viscous gel contained 16.9 parts of water and about 12.7 parts of the ethoxy-sulfonate product. On an anhydrous basis thus a 50% ethoxysulfonate mixture was concentrated to a 75% concentrate in one extraction.

The term "sulfonation," as used here is employed to describe in a short-hand manner the actual and properly termed sulfoalkylation reaction such as the sulfoethylation reaction involving sodium isethionate and an alcohol.

The invention is claimed as follows:

1. A method of preparing ether sulfonates of the formula:

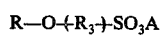

where R is a radical selected from the group consisting of $C_2$-$C_{22}$ alkyl, $C_2$-$C_{22}$ alkenyl, $C_2$-$C_{22}$ hydroxyalkyl, $C_2$-$C_{22}$ hydroxyalkenyl, alkaryl containing 1 or more $C_1$-$C_{18}$ alkyl groups substituted on said aryl group, aralkyl containing 7–28 carbon atoms, and polyalkyleneether derivatives of any of the foregoing, $R_3$ is alkylene, and A is an alkali metal cation which comprises the step of reacting in the presence of a base and in the liquid phase an alcohol having a molecular weight greater than 200 and having the formula, ROH where R has the just stated significance, with an alkali metal hydroxy-containing alkyl sulfonic acid salt under a vacuum less than about 300 mm of mercury while for at least the majority of said reaction period continuously dispersing an inert gas through said liquid reaction mass.

2. The method of claim 1 wherein said sulfonic acid salt reactant is the sodium salt of 2-hydroxyethane sulfonic acid.

3. The method of claim 1 wherein said reaction is run under a vacuum less than about 100 mm of mercury.

4. The method of claim 3 wherein said vacuum is 2–100 mm.

5. The method of claim 1 wherein said inert gas is nitrogen.

6. The method of claim 1 wherein said alcohol ROH is reacted with a sulfonic acid salt by slowly adding an aqueous solution of said salt to said alcohol at a rate less than that sufficient to agglomerate finely divided particles of said salt during said reaction.

TABLE I

| Solvent (A) | Insoluble % | Diluent (B) | Extractant (C) | Ratio, Wt. Sample Vol. A/ Vol B/ Vol C | Organic Soluble % | Water Soluble Sulfonate % | Sulfonate % | Sulfonate Recovered In Water, % |
|---|---|---|---|---|---|---|---|---|
| | 25.0 | — | — | — | 50.0 | 25.0 | 83.6 | — |
| Ethyl Acetate | 17.2 | Water | — | 1/5/2/0 | 42.4 | 26.6 | 59.1 | 75.2 |
| Acetone | 23.2 | Water | Benzene | 1/3/2/3 | 49.8 | 27.2 | 72.9 | 95.6 |
| Acetone | 17.8 | Water | Pet. Ether | 1/3/2/2 | 3.0 | 73.8 | — | — |
| Methyl Ethyl Ketone | 21.6 | Water | Pet. Ether | 1/4/1/2 | 38.3 | 29.4 | — | — |
| Benzene | 21.2 | Water | — | 1/4/2/0 | 40.6 | 32.2 | 43.1 | 67.0 |
| Toluene | 26.6 | Water | — | 1/4/2/0 | 51.8 | 28.8 | 48.6 | 67.6 |
| Methanol | 16.8 | Water | Pet. Ether | 1/4/2/2 | 3.0 | 75.8 | — | — |
| Iso-Octane | 28.8 | Water | Pet. Ether | 1/4/4/2 | Emulsion | 61.2 | — | — |
| Isopropyl Alcohol | 22.8 | Water | Pet. Ether | 1/4/2/2 | Emulsion | 71.2 | — | — |
| Chloroform | 22.8 | Water | Pet. Ether | 1/5/3/3 | Emulsion | 53.6 | — | — |

EXAMPLE 21

Here, further extraction work was done with a greatly preferred species involving a ethyl acetate-water combination.

To 25 parts of a reaction mixture containing equal molar quantities of the alcohol reactant of example 4, and sodium isethionate, and which also contained 12.5 parts of the reaction product thereof, was added 50 parts in terms of volume of water to form a solution. Upon adding 50 parts by volume of ethyl acetate and mixing, little separation occurred. By the addition of 50 additional parts of ethyl acetate for a total of 100 parts, 7. The method of claim 1 wherein said reaction is carried out at a temperature less than the melting point of said sulfonic acid salt.

8. The method of claim 1 wherein said reaction is terminated near the point of maximum conversion by cooling the reaction mass.

9. The method of claim 7 wherein said temperature of reaction is greater than 180° C.

10. The method of claim 1 where $R_3$ is ethylene or propylene.

11. The method of preparing ether sulfonates of the formula:

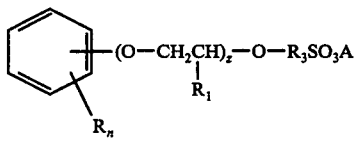

where R is a $C_1$-$C_{22}$ alkyl group, $n$ is an integer of 1-3, $R_1$ is H or $CH_3$, $z$ is an integer of 1-40, $R_3$ is ethylene or propylene and A is an alkali metal cation, which comprises the step of reacting in the presence of a base and in the liquid phase an alcohol compound having the formula

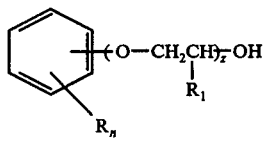

where R, $R_1$, $n$ and $z$ have a significance as above stated with a hydroxy-containing alkali metal alkyl sulfonic acid salt having the formula $$OHR_3SO_3A$$

where $R_3$ and A have the significance as above stated under a vacuum less than about 300 mm of mercury, while for at least the majority of said reaction period continuously dispersing an inert gas through said liquid reaction mass.

12. The method of claim 11 wherein said sulfonic acid salt is the sodium salt of 2-hydroxyethane sulfonic acid.

13. The method of claim 11 wherein said vacuum is less than about 100 mm.

14. The method of claim 13 wherein said vacuum is 2-100 mm.

15. The method of claim 11 wherein said inert gas is nitrogen.

16. The method of claim 11 wherein said alcohol is reacted with a sulfonic acid salt by slowly adding an aqueous solution of said salt to said alcohol at a rate less than that sufficient to agglomerate finely divided particles of said salt during said reaction.

17. The method of claim 11 wherein said reaction is carried out at a temperature less than the melting point of said sulfonic acid salt.

18. The method of claim 11 wherein said reaction is terminated near the point of maximum conversion by cooling said reaction mass.

19. The method of claim 11 wherein said temperature of reaction is greater than about 180° C.

20. The method of claim 11 wherein $R_3$ is ethylene.

21. The method of claim 20 wherein said reaction is carried out at a temperature range of about 180°-190° C.

22. The method of claim 11 wherein R is a $C_6$-$C_{20}$ alkyl group, and $n$ is 1.

23. The method of claim 22 wherein R is $C_8$-$C_{12}$.

24. The method of claim 11 wherein $z$ is 1-10.

25. The method of claim 24 where $z$ is 2-6.

26. The method of claim 11 wherein said base is potassium hydroxide.

27. The method of claim 11 wherein said base catalyzed reaction is carried out by first forming the alkoxide of said alcohol reactant.

28. The method of claim 11 wherein a molar excess of said alcohol is present during said reaction.

29. The method of claim 28 wherein 1.2-2.5 mols of said alcohol are reacted per mole sulfonic acid salt.

30. The method of claim 29 wherein 1.5-2:1 mols of said alcohol are reacted per mole of sulfonic acid salt 31. The method of claim 11 wherein unreacted alcohol is separated from said ether sulfonates by solvent extraction with a mixture of water and an organic ester.

32. The method of claim 31 wherein said organic ester is ethyl acetate.

33. The method of claim 11 wherein said ether sulfonate is separated from unreacted alcohol by solvent extraction with a mixture of water, an organic ketone and an organic hydrocarbon.

34. The method of claim 33 wherein said mixture comprises benzene, acetone and water.

* * * * *